US012758122B2

(12) United States Patent
Kiourti et al.

(10) Patent No.: US 12,758,122 B2
(45) Date of Patent: Oct. 13, 2026

(54) SYSTEMS AND METHODS FOR MEASURING GROWTH SUCH AS HEIGHT, WEIGHT, AND BMI VIA ELECTROMAGNETIC ANTENNAS PROVIDED ON A SUBSTRATE

(71) Applicant: Ohio State Innovation Foundation, Columbus, OH (US)

(72) Inventors: Asimina Kiourti, Columbus, OH (US); Lisa Militello, Columbus, OH (US)

(73) Assignee: Ohio State Innovation Foundation, Columbus, OH (US)

(*) Notice: Subject to any disclaimer, the term of this patent is extended or adjusted under 35 U.S.C. 154(b) by 585 days.

(21) Appl. No.: 18/138,884

(22) Filed: Apr. 25, 2023

(65) Prior Publication Data

US 2023/0337940 A1 Oct. 26, 2023

Related U.S. Application Data

(63) Continuation of application No. 17/353,283, filed on Jun. 21, 2021, now Pat. No. 11,684,289, which is a (Continued)

(51) Int. Cl.
*A61B 5/107* (2006.01)
*A61B 5/00* (2006.01)
*A61B 5/0507* (2021.01)

(52) U.S. Cl.
CPC .......... *A61B 5/1072* (2013.01); *A61B 5/0507* (2013.01); *A61B 5/1075* (2013.01); (Continued)

(58) Field of Classification Search
CPC ... A61B 5/1072; A61B 5/0507; A61B 5/1075; A61B 5/6814; A61B 5/6892; A61B 5/1077
See application file for complete search history.

(56) References Cited

U.S. PATENT DOCUMENTS

| | | | | |
|---|---|---|---|---|
| 2005/0235482 | A1 | 10/2005 | Deaett et al. | |
| 2010/0067770 | A1* | 3/2010 | Persson ................ | A61B 5/0507 382/132 |

(Continued)

OTHER PUBLICATIONS

P. Scherdel et al., "Growth monitoring: A survey of current practices of primary care paediatricians in Europe," PLoS ONE, vol. 8, No. 8, May 2013, Art. No. e70871.

(Continued)

*Primary Examiner* — Serkan Akar
(74) *Attorney, Agent, or Firm* — Meunier Carlin & Curfman LLC

(57) ABSTRACT

A biometric monitoring system comprises a substrate with a first surface having a length and a width. A first transmitting antenna is coupled to the first surface at a first end of the length of the first surface. A second transmitting antenna is coupled to the first surface at a second end of the length of the first surface. The first and second transmitting antennas extend across the width of the first surface. A plurality of receiving antennas are coupled to the first surface, each of which extends across the width of the substrate and is spaced apart from an adjacent receiving antenna along the length by a predetermined distance. A controller is configured to supply a first signal to the first transmitting antenna and sequentially measure a transmission coefficient or voltage of the first signal at the plurality of receiving antennas until an attenuation in the transmission coefficient or voltage exceeds a threshold.

8 Claims, 7 Drawing Sheets

Related U.S. Application Data continuation of application No. 16/285,642, filed on Feb. 26, 2019, now Pat. No. 11,039,759.

(60) Provisional application No. 62/635,249, filed on Feb. 26, 2018.

(52) U.S. Cl.
CPC .......... *A61B 5/6814* (2013.01); *A61B 5/6892* (2013.01); *A61B 5/1077* (2013.01)

(56) References Cited

U.S. PATENT DOCUMENTS

| | | | | |
|---|---|---|---|---|
| 2012/0190977 | A1* | 7/2012 | Persson | G06F 18/2135 342/146 |
| 2013/0248226 | A1* | 9/2013 | Sime | H05K 1/038 156/247 |
| 2014/0298667 | A1 | 10/2014 | Alkhalaf | |
| 2018/0368733 | A1 | 12/2018 | Kimura et al. | |
| 2019/0101415 | A1 | 4/2019 | Sekeljic et al. | |

OTHER PUBLICATIONS

S. Carsley, C. S. Birken, K. Tu, E. Pullenayegum, and P. C. Parkin, "Examining growth monitoring practices for children in primary care," Archives Dis. Childhood, 2017, 6 pages. doi: 10.1136/archdischild-2017-314016.

L. Savendahl and M. L. Davenport, "Delayed diagnoses of Turner's syndrome: Proposed guidelines for change," J. Pediatrics, vol. 137, No. 4, pp. 455-459, 2000.

M. Gasparetto, "Crohns disease and growth deficiency in children and adolescents," World J. Gastroenterol., vol. 20, No. 37, pp. 13219-13233, 2014.

D. Craig, D. Fayter, L. Stirk, and R. Crott, "Growth monitoring for short stature: Update of a systematic review and economic model," Health Technol. Assessment, vol. 15, No. 11, 2011.

C. R. Kahrs, M. C. Magnus, H. Stigum, K. E. A. Lundin, and K. Størdal, "Early growth in children with coeliac disease: A cohort study," Archives Dis. Childhood, vol. 102, No. 11, pp. 1037-1043, 2017.

"Recommendations for growth monitoring, and prevention and management of overweight and obesity in children and youth in primary care," Can. Med. Assoc. J., vol. 187, No. 6, pp. 411-421, 2015.

P. Mahachoklertwattana, C. Preeyasombat, L. Choubtum, and A. Sriphrapradang, "Final height after long-term growth hormone treatment in Thai children with turner syndrome," Hormone Res., vol. 49, No. Suppl. 1, pp. 55-55, 1998.

G. C. A. Gascoin-Lachambre, R. Brauner, L. Duche, and M. Chalumeau, "Pituitary stalk interruption syndrome: Diagnostic delay and sensitivity of the auxological criteria of the growth hormone research society," PLoS ONE, vol. 6, No. 1, 2011, Art. No. e16367.

R. W. Holl, D. Kunze, H. Etzrodt, W. Teller, and E. Heinze, "Turner syndrome: Final height, glucose tolerance, bone density and psychosocial status in 25 adult patients," Eur. J. Pediatrics, vol. 153, No. 1, pp. 11-16, 1994.

P. L. Selby, M. Davies, J. E. Adams, and E. B. Mawer, "Bone loss in celiac disease is related to secondary hyperparathyroidism," J. Bone Mineral Res., vol. 14, No. 4, pp. 652-657, Jan. 1999.

M. D. Onis, A. W. Onyango, J. V. D. Broeck, C. W. Chumlea, and R. Martorell, "Measurement and standardization protocols for anthropometry used in the construction of a new international growth reference," Food Nutrition Bull., vol. 25, pp. S27-S36, 2004.

L. R. Braun and R. Marino, "Disorders of growth and stature," Pediatrics Rev., vol. 38, No. 7, pp. 293-304, 2017.

R. J. Kuczmarski et al., "2000 CDC growth charts for the United States: methods and development," Vital Health. Stat., vol. 246, pp. 1-190, May 2002.

D. Giovenale et al., "The prevalence of growth hormone deficiency and celiac disease in short children," Clin.Med. Res., vol. 4, No. 3, pp. 180-183, Jan. 2006.

"Well-Child Visits," Well-Child Visits, Child Health USA 2014. (Aug. 20, 2014). [Online]. Available: https://mchb.hrsa.gov/chusa14/healthservices-financing-utilization/well-child-visits.html. Accessed Nov. 30, 2017.

U. Sankilampi, A. Saari, T. Laine, P. J. Miettinen, and L. Dunkel, "Use of electronic health records for automated screening of growth disorders in primary care," JAMA, vol. 310, No. 10, pp. 1071-1072, Nov. 2013.

A. Islam, A. Kiourti, and J. L. Volakis, "A microwave tomographic technique to enhance real-imaginary permittivity image quality," in Proc. IEEE Int. Symp. Antennas Propag., San Diego, CA, USA, Jul. 9-15, 2017, pp. 2363-2364.

S. Salman,A.Kiourti, and J. L. Volakis, "Rudimentary deep tissue imaging through awearable real-timemonitoring system," in Proc. IEEE Int. Symp. Antennas Propag., Vancouver, BC, Canada, Jul. 19-25, 2015, pp. 729-729.

L. D. Howe, K. Tilling, and D. A. Lawlor, "Accuracy of height and weight data from child health records," J. Epidemiol. Commun. Health, vol. 63, No. Suppl 2, pp. 79-79, Sep. 2009.

K. Chan and D. Means, "Evaluating compliance with FCC guidelines for human exposure to radiofrequency electromagnetic fields," OET Bull. 65, vol. Suppl C, Edition 97-01, 57 pages, 1997.

C. W. L. Lee, A. Kiourti, J. Chae, and J. L. Volakis, "A high-sensitivity fully passive neurosensing system for wireless brain signal monitoring," IEEE Trans. Microw. Theory Techn., vol. 63, No. 6, pp. 2060-2068, Jun. 2015.

A. Kiourti and J. L. Volakis, "Stretchable and flexible e-fiber wire antennas embedded in Polymer," IEEE Antennas Wireless Propag Lett., vol. 13, pp. 1381-1384, 2014.

A. Kiourti and J. L. Volakis, "Colorful textile antennas integrated into embroidered logos," J. Sens. Actuator Netw., vol. 4, No. 4, pp. 371-377, Aug. 2015.

J. Zhong, A. Kiourti, T. Sebastian, Y. Bayram, and J. L. Volakis, "Conformal load-bearing spiral antenna on conductive textile threads," IEEE Antennas Wireless Propag. Lett., vol. 16, 4 pages, 2017.

A. Kiourti, C. Lee, and J. L. Volakis, "Fabrication of textile antennas and circuits with 0.1 mm precision," IEEE Antennas Wireless Propag. Lett., vol. 15, pp. 151-153, 2016.

M. L. Scarpello, I. Kazani, C. Hertleer, H. Rogier, and D. V. Ginste, "Stability and efficiency of screen-printed wearable and washable antennas," IEEE Antennas Wireless Propag. Lett., vol. 11, pp. 838-841, 2012.

A. Kazmi, M. Rizwan, L. Sydanheimo, L. Ukkonen, and J. Virkki, "A reliability study of coating materials for brush-painted washable textile RFID tags," in Proc. 6th Electron. Syst.-Integr. Technol. Conf., pp. 1-4, 2016.

C. Hertleer, A. V. Laere, H. Rogier, and L. V. Langenhove, "Influence of relative humidity on textile antenna performance," Textile Res. J., vol. 80, No. 2, pp. 177-183, 2009.

X. Jia, A. Tennant, R. Langley, W. Hurley, and T. Dias, "Moisture effects on a knitted waveguide," in Proc. Loughborough Antennas Propag. Conf., pp. 1-3, 2016.

J. Kim and Y. Rahmat-Samii, "Implanted antennas inside a human body: Simulations, designs, and characterizations," IEEE Trans. Microw. Theory Techn., vol. 52, No. 8, pp. 1934-1943, Aug. 2004.

T. K. McInerny, "Reassessment of exposure to radiofrequency electromagnetic fields limits and policies," Fed. Reg., vol. 78, No. 107, pp. 33654-33687, Jun. 2013.

U.S. Govt. Accountability Office. "Telecommunications: Exposure and Testing Requirements for Mobile Phones Should be Reassessed," Aug. 2012. [Online]. Available: http://www.gao.gov/products/GAO-12-771. Accessed Sep. 8, 2015.

M. Martinez-Burdalo, A. Martin, M. Anguiano, and R. Villar, "Comparison of FDTD-calculated specific absorption rate in adults and children when using a mobile phone at 900 and 1800 MHZ," Phys. Med. Biol., vol. 49, No. 2, pp. 345-354, May 2004.

R. D. Morris, L. L. Morgan, and D. Davis, "Children absorb higher doses of radio frequency electromagnetic radiation from mobile phones than adults," IEEE Access, vol. 3, pp. 2379-2387, 2015.

(56) References Cited

OTHER PUBLICATIONS

Zhu, et al., Antenna-Impregnated Fabrics for Recumbent Height Measurement on the Go, IEEE Journal of Electromagnetics, Rf, and Microwaves in Medicine and Biology, vol. 2, No. 1, Mar. 2018, 33-39.

* cited by examiner

SYSTEMS AND METHODS FOR MEASURING GROWTH SUCH AS HEIGHT, WEIGHT, AND BMI VIA ELECTROMAGNETIC ANTENNAS PROVIDED ON A SUBSTRATE

CROSS REFERENCE TO RELATED APPLICATIONS

This application is a continuation of U.S. Ser. No. 17/353,283, filed Jun. 21, 2021, issued as U.S. Pat. No. 11,684,289 on Jun. 27, 2023, which is a continuation of U.S. Ser. No. 16/285,642, filed Feb. 26, 2019, issued as U.S. Pat. No. 11,039,759 on Jun. 22, 2021, which claims priority to U.S. Provisional Patent Application Ser. No. 62/635,249 filed Feb. 26, 2018, the disclosures of which are expressly incorporated herein by reference.

BACKGROUND

Recent studies indicate an increasing need for monitoring human height on a regular basis, particularly for assessing children's health in their early years. Growth monitoring may help to early identify conditions that include, but are not limited to, Turner syndrome, Crohn's disease, growth hormone deficiency (GHD), short stature, Celiac disease, and obesity. Notably, failure to identify/treat these conditions at an early stage is known to increase the risk for several other health implications in future such as short stature, high body mass index, low glucose tolerance, distress, osteoporotic bone loss, etc.

Existing practices for monitoring children's height rely on manual, time-consuming, inefficient, and rather cumbersome measurements. As an example, the standard height measurement process for children under 24 months entails the use of an infantometer. The latter requires two anthropometrists to record the height of a child: one keeps the child's head snugly so that it touches a fixed vertical plank, while the other presses over the knees, places a second moveable plank at the end of the feet, and records the height. At older ages, height is typically measured using a tape measure or a stadiometer. Though straightforward and simple, these methods are still time-consuming and prone to measurement errors. The American Academy of Pediatrics recommends monitoring children's height per a periodicity schedule. Such data should, eventually, be compared with the World Health Organization growth standards (0-2 years old) or the Centers for Disease Control and Prevention growth charts (>2 years old) to identify abnormal growth. Depending on the diagnosis, a treatment plan is finally employed that should, in turn, involve regular (per case) height monitoring (e.g., at least 4 times per year for GHD therapy). However, in practice, the proportion of well-child visits declines with age, and is far less for uninsured children. Thus, current approaches to regularly monitor height are inefficient.

SUMMARY

In a first aspect of the disclosure, a biometric monitoring system comprises a substrate with a first surface having a length and a width. The biometric monitoring system also comprises a first transmitting antenna coupled to the first surface at a first end of the length of the first surface. The first transmitting antenna extends across the width of the first surface. The biometric monitoring system also comprises a second transmitting antenna coupled to the first surface at a second end of the length of the first surface. The second transmitting antenna extends across the width of the first surface. The biometric monitoring system also comprises a plurality of receiving antennas coupled to the first surface. Each of the plurality of receiving antennas extends across the width of the substrate and is spaced apart from an adjacent receiving antenna along the length by a predetermined distance. The biometric monitoring system also comprises a controller configured to supply a first signal to the first transmitting antenna and sequentially measure a transmission coefficient or voltage of the first signal at the plurality of receiving antennas starting from a receiving antenna closest to the first end until a difference between the transmission coefficient or voltage of the first signal and an expected transmission coefficient or voltage of the first signal is greater than a threshold difference at a first of the plurality of receiving antennas.

In some implementations of the first aspect of the disclosure, the second transmitting antenna is one of the plurality of receiving antennas when the first transmitting antenna is transmitting the first signal.

In some implementations of the first aspect of the disclosure, the controller is further configured to supply a second signal to the second transmitting antenna and sequentially measure a transmission coefficient or voltage of the second signal at the plurality of receiving antennas starting from a receiving antenna closest to the second end until a difference between the transmission coefficient or voltage of the second signal and an expected transmission coefficient or voltage of the second signal is greater than the threshold difference at a second of the plurality of receiving antennas.

In some implementations of the first aspect of the disclosure, the first transmitting antenna is one of the plurality of receiving antennas when the second transmitting antenna is transmitting the second signal.

In some implementations of the first aspect of the disclosure, the controller is further configured to determine a length of an object placed on the substrate based on a location of the first and second of the plurality of receiving antennas.

In some implementations of the first aspect of the disclosure, the length is determined based on the predetermined distance and a difference between a first length value of the first of the plurality of receiving antennas from a reference location and a second length value of the second of the plurality of receiving antennas from the reference location.

In some implementations of the first aspect of the disclosure, the plurality of receiving antennas are offset fed dipole antennas.

In some implementations of the first aspect of the disclosure, the substrate comprises a second surface having the length and the width. The biometric monitoring system further comprises a conductive ground plane coupled to the second surface.

In some implementations of the first aspect of the disclosure, the substrate is a fluid-filled cavity with a pressure sensor at a fluid port for the cavity. The controller is further configured to determine a weight of the object based on a difference between a pressure measured by the pressure sensor and a baseline pressure measurement.

In some implementations of the first aspect of the disclosure, the biometric monitoring system further comprises a user interface comprising a plurality of buttons. Each of the plurality of buttons corresponding to a different mood, wherein the controller is further configured to receive a mood signal corresponding to a selected one of the plurality of buttons.

In some implementations of the first aspect of the disclosure, the biometric monitoring system further comprises a third transmitting antenna coupled to the first surface at a third end of the width of the first surface. The third transmitting antenna extends across the length of the first surface. The biometric monitoring system further comprises a second plurality of receiving antennas coupled to the first surface. Each of the second plurality of receiving antennas extends across the length of the substrate and is spaced apart from an adjacent second receiving antenna along the width by a second predetermined distance.

In some implementations of the first aspect of the disclosure, the controller is configured to determine the expected transmission coefficient or voltage of the first signal based on a measurement of a baseline transmission coefficient or voltage of the first signal when no object is present on the substrate.

A second aspect of the disclosure provides a biometric monitoring method comprising transmitting a first signal from a first transmitting antenna coupled to a first surface of a substrate. The first surface of the substrate having a length and a width. The first transmitting antenna is located at a first end of the length of the first surface and extends across the width of the first surface. The biometric monitoring method comprising sequentially measuring a transmission coefficient or voltage of the first signal at a plurality of receiving antennas on the substrate starting from a receiving antenna closest to the first end. Each of the plurality of receiving antennas extends across the width of the substrate and is spaced apart from an adjacent receiving antenna along the length by a predetermined distance. The biometric monitoring method comprising identifying a first of the plurality of receiving antennas where a difference between the transmission coefficient or voltage of the first signal and an expected transmission coefficient or voltage of the first signal is greater than a threshold difference.

In some implementations of the second aspect of the disclosure, the biometric monitoring method further comprises transmitting a second signal from a second transmitting antenna coupled to the first surface of the substrate. The second transmitting antenna located at a second end of the length of the first surface and extends across the width of the first surface. The biometric monitoring method further comprises sequentially measuring a transmission coefficient or voltage of the second signal at the plurality of receiving antennas on the substrate starting from a receiving antenna closest to the second end. The biometric monitoring method further comprises identifying a second of the plurality of receiving antennas where a difference between the transmission coefficient or voltage of the second signal and an expected transmission coefficient or voltage of the second signal is greater than the threshold difference.

In some implementations of the second aspect of the disclosure, the biometric monitoring method further comprises determining a length of an object placed on the substrate based on a location of the first and second of the plurality of receiving antennas.

In some implementations of the second aspect of the disclosure, the length is determined based on the predetermined distance and a difference between a first length value of the first of the plurality of receiving antennas from a reference location and a second length value of the second of the plurality of receiving antennas from the reference location.

In some implementations of the second aspect of the disclosure, the substrate is a fluid-filled cavity with a pressure sensor at a fluid port for the cavity, the biometric monitoring method further comprises determining a weight of the object based on a difference between a pressure measured by the pressure sensor and a baseline pressure measurement.

In some implementations of the second aspect of the disclosure, the biometric monitoring method further comprises determining the expected transmission coefficient or voltage of the first signal based on a measurement of a baseline transmission coefficient or voltage of the first signal when no object is present on the substrate.

In some implementations of the second aspect of the disclosure, the biometric monitoring method further comprises receiving a mood signal corresponding to a selected one of a plurality of buttons on a user interface coupled to the substrate.

In some implementations of the second aspect of the disclosure, the biometric monitoring method further comprises transmitting a third signal from a third transmitting antenna coupled to the first surface of the substrate. The third transmitting antenna located at a third end of the width of the first surface and extends across the length of the first surface. The biometric monitoring method further comprises sequentially measuring a transmission coefficient or voltage of the third signal at a second plurality of receiving antennas on the substrate starting from a second receiving antenna closest to the third end. Each of the plurality of second receiving antennas extends across the length of the substrate and is spaced apart from an adjacent second receiving antenna along the width by a second predetermined distance. The biometric monitoring method further comprises identifying a first of the plurality of second receiving antennas where a difference between the transmission coefficient or voltage of the third signal and an expected transmission coefficient or voltage of the third signal is greater than the threshold difference.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

It should be understood at the outset that although illustrative implementations of one or more embodiments are illustrated below, the disclosed systems and methods may be implemented using any number of techniques, whether currently known or in existence. The disclosure should in no way be limited to the illustrative implementations, drawings, and techniques illustrated below, but may be modified within the scope of the appended claims along with their full scope of equivalents. Use of the phrase "and/or" indicates that any one or any combination of a list of options can be used. For example, "A, B, and/or C" means "A", or "B", or "C", or "A and B", or "A and C", or "B and C", or "A and B and C".

An automated way of unobtrusively monitoring height or length on a regular basis would offer unprecedented opportunities in monitoring children's growth and providing early detection/prevention of related disorders. A biometric monitoring sensor, such as an antenna-impregnated fabric, provides for wireless recumbent length monitoring. In brief, the proposed fabric includes multiple dipole antennas placed at known intervals/distances from each other. The two antennas placed at the ends of the fabric are transmitting (one at a time), while the rest are receiving. When a subject is lying upon the fabric, they detune the underlying antennas, inducing losses in the associated wireless transmission paths. Therefore, the subject's length can be calculated by identifying the two antennas with degraded transmission coefficients at the starting point (head) and ending point (feet) of the human body, respectively. In some implementations, instead of measuring the transmission coefficients, the transmitted and received voltages may be measured.

Within the pediatric clinical practice, measures of length or height for children are documented on a growth chart to illustrate the body measure distribution in a series of percentile curves. Health care providers typically utilize the World Health Organization (WHO) growth standards and/or the Centers for Disease Control and Prevention (CDC) growth charts to monitor growth in infants and children. In general, measurements taken while the child is lying down (recumbent) are "length" whereas "height" is measured while the child is standing upright. Children less than two years of age are traditionally measured in the recumbent position (length), while height is used for children two years and older who are able to stand. To convert recumbent length to height, the recumbent length measurement may be subtracted by 0.7 cm. The most current WHO length/height-for-age growth chart documents to the nearest centimeter (cm). Current CDC charts reflect length and height by ½ inch increments, which is equivalent to 1.27 cm increments.

Figure 1:
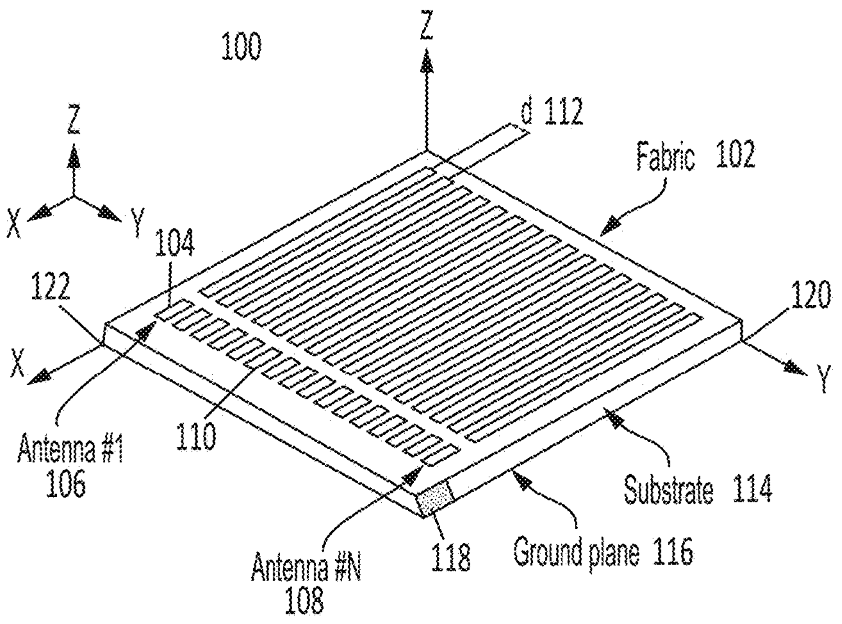
FIG. 1 is a biometric monitoring sensor suitable for implementing the several embodiments of the disclosure.

FIG. 1 is a biometric monitoring sensor 100 suitable for implementing the several embodiments of the disclosure. The biometric monitoring sensor 100 comprises an antenna-impregnated fabric 102 with an array of antennas 104. The antenna-impregnated fabric 102 has a length 120 and a width 122. The array of antennas 104 comprise a first transmitting antenna 106 positioned at a first end of the antenna-impregnated fabric 102, a second transmitting antenna 108 positioned at second end of the antenna-impregnated fabric 102, and a plurality of receiving antennas 110 positioned therebetween. The two transmitting antennas 106, 108 are at the opposite ends of the antenna-impregnated fabric 102 and are operated as described below to transmit a signal, one at a time, while the rest of the antennas in the array 104 are receiving. Each of the antennas in the array of antennas 104 is spaced apart from one another by a predetermined distance 112. In the example shown, the antennas in the array of antennas 104 each extend across the width 122 of the antenna-impregnated fabric 102 and are separated from each other by the predetermined distance 112 in a direction of the length 120.

While described as a fabric, the antenna-impregnated fabric 102 includes any flexible or rigid non-conducting surface upon which the array of antennas 104 may be affixed, deposited, taped, glued, weaved, or otherwise attached. In some examples, the surface may be a polymer, textile, ceramic, or other such surface with which the array of antennas 104 may be attached. In some examples, the antennas may be provided by a conductive metal tape, an E-thread, a conductive trace, a wire, or any other suitable antenna material.

In various implementations, the antennas in the array of antennas 104 are dipole antennas. In order to enlarge the surface area where the subject may lie upon the fabric for recumbent length measurement, asymmetric feeds are selected for the antennas (i.e., one dipole arm is longer than the other). In various implementations, other antennas or feed arrangements may be used, such as end-fed antennas.

The antenna-impregnated fabric 102 may be affixed to a surface (e.g., top surface) of the substrate 114. The surface of the substrate 114 may have the same length 120 and width 122 as the antenna-impregnated fabric 102. The substrate 114 may provide additional structure and stability to the antenna-impregnated fabric 102. For example, when the antenna-impregnated fabric 102 is constructed of flexible materials, the substrate 114 prevents the antenna-impregnated fabric 102 from wrinkling or otherwise allowing the predetermined distance 112 to be changed. Additionally, for a recumbent length measurement, the substrate 114 may provide a more comfortable surface upon which a subject may lie. In some examples, the substrate 114 may be a flexible foam or a fluid-filled cavity (e.g., air mattress).

A ground plane 116 is added underneath the antenna-impregnated fabric 102 to avoid any disturbance from the per-case underlying surface (e.g., fabric lying upon a wooden vs. metal-based surface). The ground plane 116 may be affixed to a surface (e.g., a bottom surface) of the substrate 114.

As described in detail below, the biometric monitoring sensor 100 may be operated to generate a recumbent length measurement for a subject. Additional biometric sensors may be incorporated into the antenna-impregnated fabric 102 and/or the substrate 114 for providing additional measurements of the subject. For example, when the substrate 114 is a fluid-filled cavity, a pressure sensor 118 is provided at a fluid port for the cavity. Based on a difference between a pressure measurement determined by the pressure sensor 118 when the subject is present and a baseline pressure measurement, a weight of the subject may be determined.

A resolution of the recumbent length measurement for the subject is defined by the predetermined distance 112 between antennas in the array of antennas 104. However, there is a trade-off between computation time and resolution that may be optimized for each particular application. For example, the error range of currently used height monitoring techniques for children is at about a 1 cm resolution. Of course, denser antenna placement can be implemented to realize higher resolution. For higher resolution applications, the cost and/or complexity of the biometric monitoring sensor 100 may increase with the increase number of antennas in the array of antennas 104. For example, to achieve a resolution of 0.5 cm, the number of antennas in the array of antennas 104 would be doubled as compared to that to achieve the 1 cm resolution.

The biometric monitoring sensor 100 can be integrated into several usage scenarios for recumbent length monitoring. Examples include: a) bed sheets that unobtrusively collect digital length data for children; b) smart baby cribs that monitor baby growth on a continuous basis; c) rollable mats that can be hang on the wall to measure height or placed upon the floor to measure the length of the overlying subject, etc. For young children, the process of maintaining a straight posture, as required for height measurement via the proposed technique, is straightforward. For infants, assistance will still be needed to some extent. However, instead of two anthropometrists currently needed to operate an infantometer, only one person will now be required, while the measurement can further be performed inside a home rather than a clinical environment. In some implementations, the biometric monitoring sensor 100 could collect measurements throughout a subject's sleep, and eventually record length as the largest value measured, e.g., overnight (assuming that the subject changes postures during sleep, the longest dimension recorded would be that of the subject in a straight position). The collected data can be wirelessly transmitted (e.g., through Bluetooth or other wireless communication protocol) to a nearby cell phone, laptop, or other computing device. Regular monitoring of a subject's length/height may provide early detection of length/height related disorders.

Variations of the biometric monitoring sensor 100 are contemplated by this disclosure. For example, in the example shown, a single array of antennas 104 is shown that extend across the width 122 and are separated from each other by the predetermined distance 112 in a direction of the length 120 of the antenna-impregnated fabric 102. In some implementations of the biometric monitoring sensor 100, one or more additional arrays of antennas may be incorporated on the antenna-impregnated fabric 102. For example, to provide both length and width measurements by the biometric monitoring sensor 100 a second array of antennas (not shown) may be incorporated on the antenna-impregnated fabric 102 such that they extend across the length 120 and are separated from each other by a second predetermined distance in a direction of the width 122. Alternatively or additionally, a second antenna-impregnated fabric (not shown) may overlay the antenna-impregnated fabric 102 and have antennas oriented at an angle (e.g., 45°, 90°, etc.) to the antennas of the antenna-impregnated fabric 102.

Figure 2:
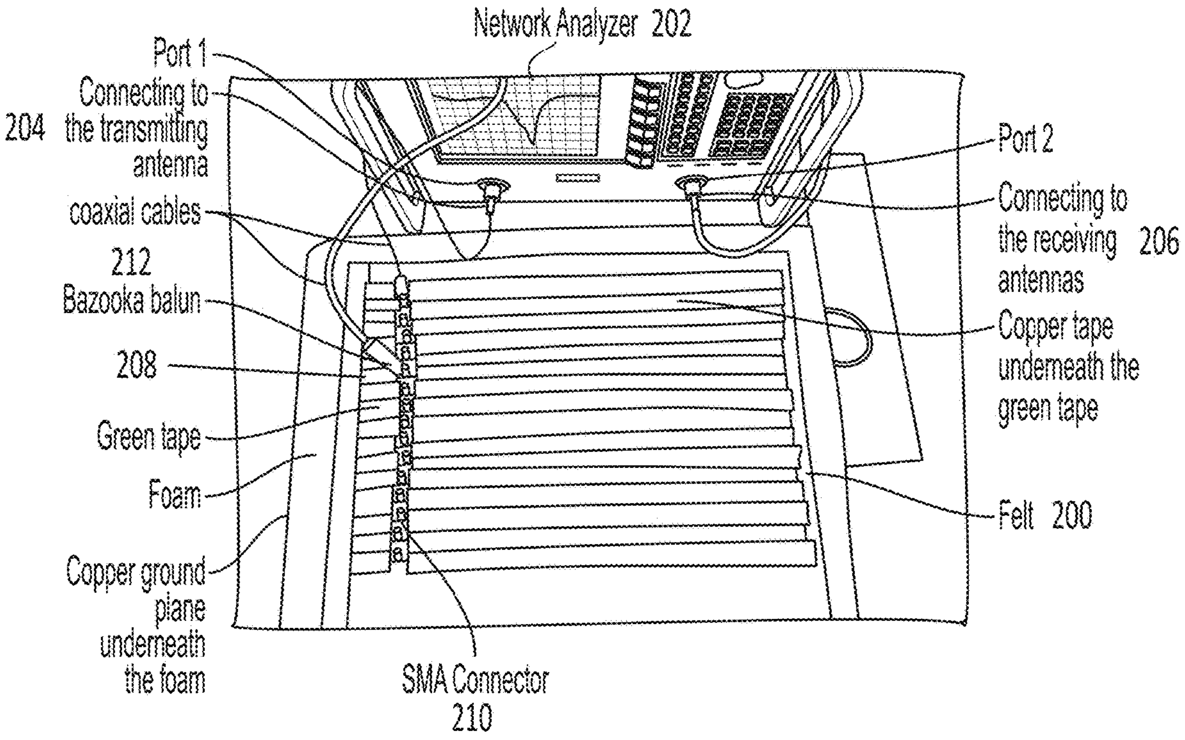
FIG. 2 is a prototype of the biometric monitoring sensor.

FIG. 2 is a prototype fabric 200 of the biometric monitoring sensor 100. The fabric 200 has a 52 cm width 122 and a 43 cm length 120 and has 16 dipole antennas in the array of antennas 104 with the predetermined distance 112 between antennas at 2 cm apart. The antenna spacing implies a 2-cm-resolution in retrieving the height/length of a subject/phantom placed upon the fabric 200. The antenna-impregnated fabric 102 comprises felt ($\varepsilon_r$=1.45, $\sigma\approx0$ S/m) with copper tape forming the antennas of the array of antennas 104. The thickness of the felt fabric is 2 mm. Green tape, with properties similar to free-space, was used to secure the copper tape antennas to the felt fabric to avoid potential delamination. The substrate 114 is composed of a flexible foam ($\varepsilon_r\approx1$, $\sigma\approx0$ S/m). Copper tape was used to provide the ground plane 116.

Transmission coefficient measurements for the prototype fabric 200 were obtained using a 2-port network analyzer 202 connected to the corresponding dipole antennas via coaxial cables. As noted above, instead of or in addition to transmission coefficient measurements, voltage measurements may be used. The output power for the network analyzer 202 was set to −30 dBm (10 μW). In the example shown, a first port 204 of the network analyzer 202 is connected to the transmitting antenna, while a second port 206 is connected to the receiving antennas 110 one at a time, such as a receiving antenna 208. For the prototype fabric 200, SMA connectors 210 were soldered to each of the antenna feed ports. Other antenna feed ports are contemplated by this disclosure. Upon connection to the second port 206, the SMA connector 210 of the corresponding one of the receiving antennas 110 (e.g., receiving antenna 208) is further connected to a bazooka baluns 212 for enabling unbalanced operation. Loads of 50Ω were connected to each of the "open" antenna feed ports of the receiving antennas 110 to prevent them from re-radiating.

For wireless operation, the first port 204 is configured to produce a signal in the 915 MHz band. The 915 MHz band was selected because it is an Industrial, Scientific, and Medical (ISM) applications band and its associated wavelength ensures a reasonable dipole length for the intended application (i.e., the antennas should be long enough to be covered by the overlying phantom, while still ensuring a reasonable size for the overall fabric). Other wireless transmission bands are contemplated by this disclosure, such as frequencies between 800 MHz and 1 GHz.

Testing of the prototype fabric 200, described in more detail below, was performed with a liquid phantom that was prepared that emulated the average human body properties at 915 MHz ($\varepsilon_r$=56.8, $\sigma$=1.07 S/m). The phantom comprised water, salt, sugar, Hydroxyethyl Cellulose (HEC), and bactericide, as shown in Table I. To accurately emulate a corresponding simulation scenario, the phantom occupied 16 cm×16 cm×1 cm (covering eight antennas upon the fabric).

TABLE I

| Ingredients | % by weight |
|---|---|
| Water | 56.0 |
| Salt (NaCl) | 0.76 |
| Sugar | 41.76 |
| HEC | 1.21 |
| Bactericide | 0.27 |

While the prototype fabric 200 is shown with copper tape placed on a felt fabric, textile-based antennas could be directly embroidered upon the fabric. For example, E-textile prototypes exhibit the same RF performance as that of their copper equivalents. As such, the prototype fabric 200 may instead comprise dipole embroidery via E-threads. Also, the fabric may be coated with breathable thermoplastic polyurethane to overcome potential issues associated with moisture trapping. Only a minor fine-tuning of the antenna design is anticipated to take the thermoplastic polyurethane into account.

Figure 3:
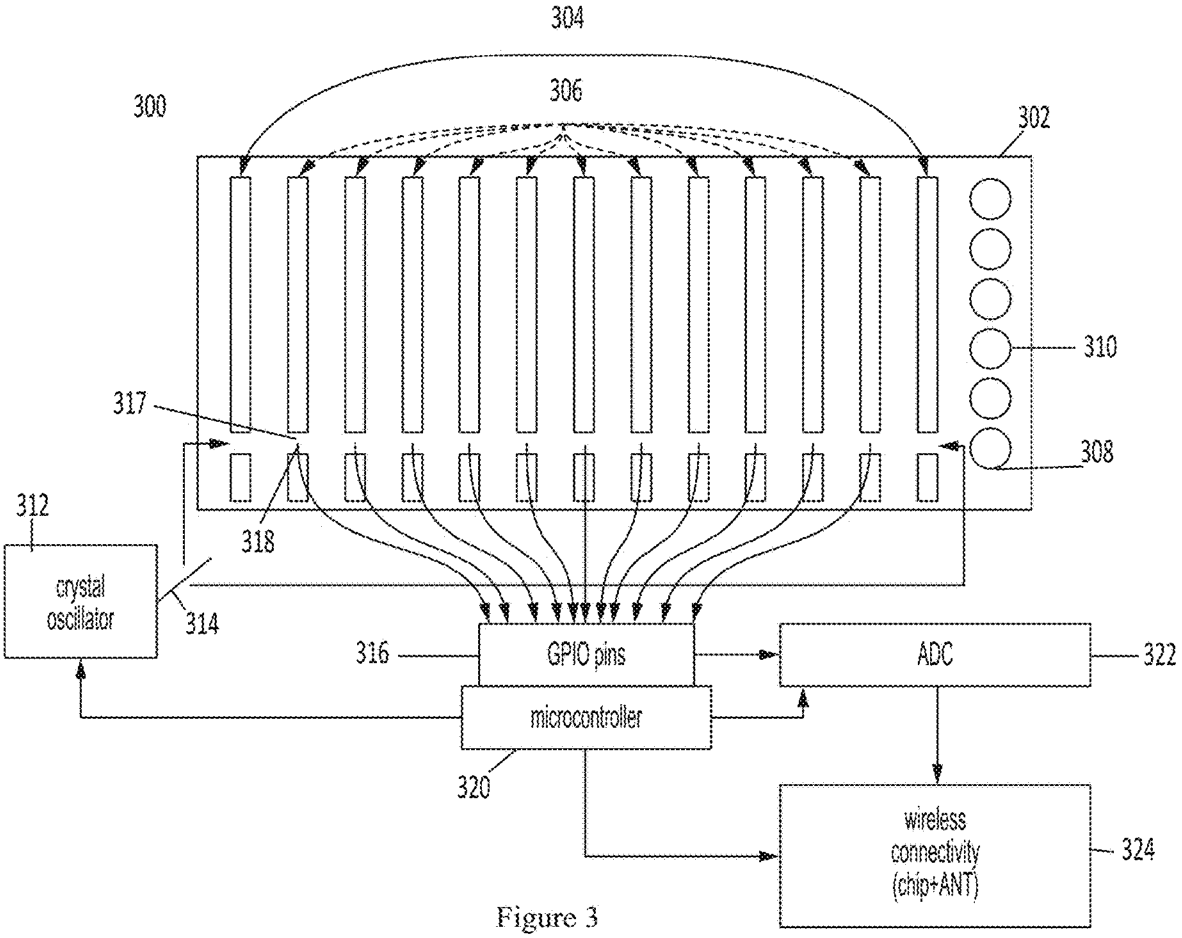
FIG. 3 is a block diagram of a biometric monitoring system suitable for implementing the several embodiments of the disclosure.

FIG. 3 is a block diagram of a biometric monitoring system 300 suitable for implementing the several embodiments of the disclosure. The biometric monitoring system 300 includes a biometric monitoring sensor 302, such as the biometric monitoring sensors 100, 200 described above. The biometric monitoring sensor 302 comprises two transmitting dipole antennas 304 and a plurality of receiving dipole antennas 306 positioned therebetween. The biometric monitoring sensor 302 additionally includes a user interface 308 comprising a plurality of mood buttons, such as a mood button 310. Upon selection of the mood button 310 on the user interface 308, a mood signal may be recorded corresponding with the selected button. For example, each of the mood buttons on the user interface 308 may correspond with a different mood of a subject, such as angry, sat, neutral, happy or other such mood observations. Therefore, in addition to length/height and weight, a regular record of mood may be recorded for the subject.

A signal generator 312, such as a crystal oscillator, provides a transmission signal to each of the transmitting antennas 304, one at a time. For example, a switch 314 may alternately connect each of the transmitting antennas 304 for transmitting the transmission signal, as described in more detail below. A set of general purpose input/output (GPIO) pins 316 may be connected to the feed points 317 of each of the receiving dipole antennas 306 via corresponding connectors 318. As described above, the connectors 318 may connect to an SMA connector at each of the feed points 317 and one or more baluns and resistive loads may be provided.

A microcontroller 320 may control operation of biometric monitoring system 300. For example, the microcontroller 320 may control operation of the switch 314 to select which one of the transmitting antennas 304 to connect to the signal generator 312 at a given time. The microcontroller may also control supplying signals read by the GPIO pins 316 to an analog-to-digital converter (ADC) 322. The digitized antenna readings may be communicated via a wireless modem 324 to an external device (not shown), such as a cellular phone, laptop, or other computing device for processing the readings from the biometric monitoring sensor 302 for determining a length/height, weight, mood, or other biometric reading of a subject.

Figure 4:
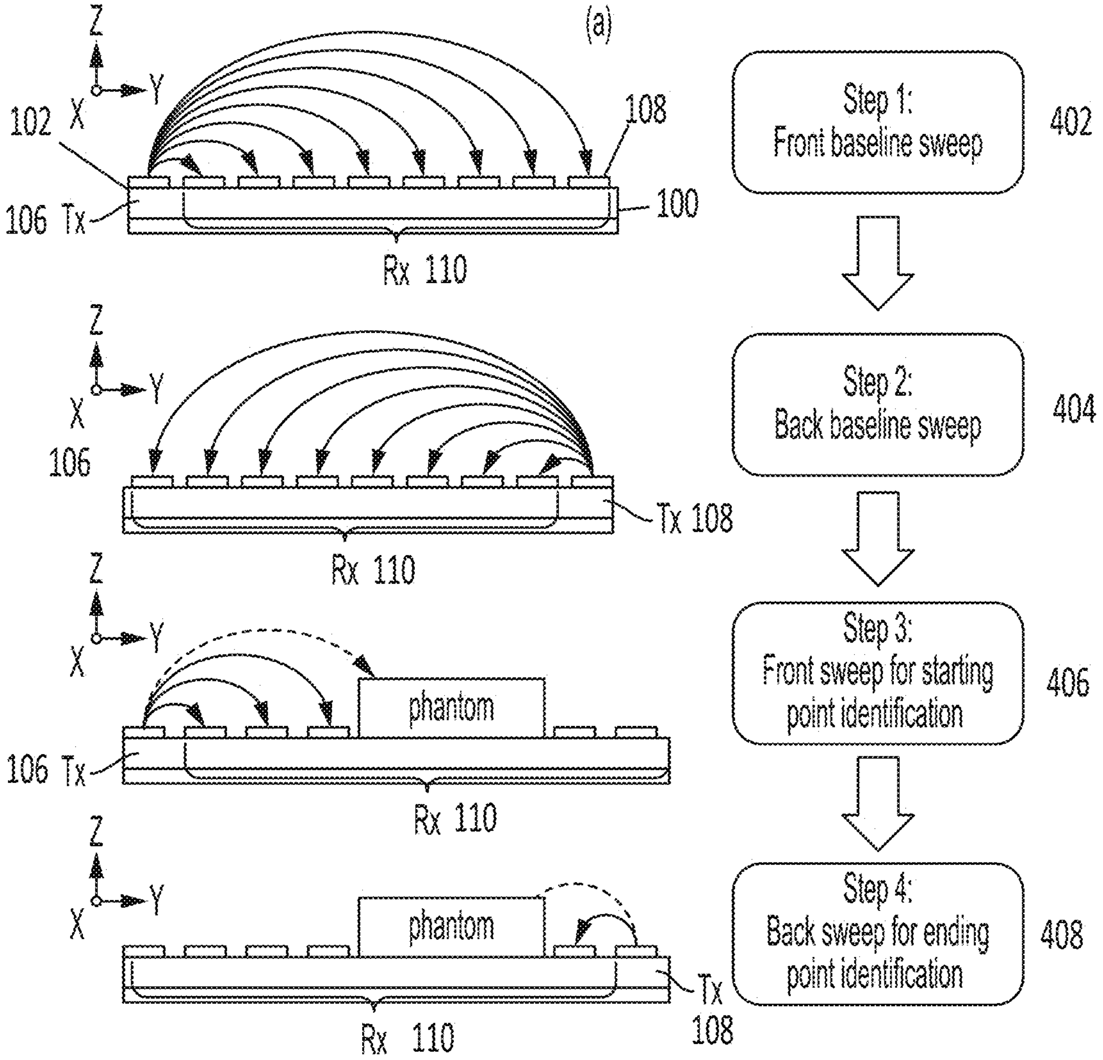
FIG. 4 is an operational flow diagram of the biometric monitoring sensor.

FIG. 4 is an operational flow diagram of the biometric monitoring sensor 100. When a subject/phantom is placed on top of the biometric monitoring sensor 100, the subject/phantom will detune the underlying antennas, inducing losses in the associated wireless transmission paths. Therefore, the subject's length (or, equivalently, the phantom's length) can be calculated by identifying the two antennas with degraded transmission coefficients or voltages at the starting point (head) and ending point (feet) of the human body, respectively.

As shown in FIG. 4, length measurement via the antenna-impregnated fabric 102 is enabled via a four-step process. At 402, a front baseline sweep is performed. The front baseline sweep is performed without the presence of any subject/phantom upon the biometric monitoring sensor 100. In the front baseline sweep, the first transmitting antenna 106 is transmitting, while the rest of the antennas in the array of antennas 104 are receiving. For example, the receiving antennas 110 are receiving and, in some implementations, the second transmitting antenna 108 may also be receiving during the front baseline sweep. In doing so, a set of front-scan baseline transmission coefficient values or voltage values S are obtained, including $|S_{2,1}|_b$, $|S_{3,1}|_b$ . . . $|S_{N,1}|_b$.

At 404 a back baseline sweep is performed. The back baseline sweep is again performed without the presence of any subject/phantom upon the biometric monitoring sensor 100. In the back baseline sweep, the second transmitting antenna 108 is transmitting, while the rest of the antennas in the array of antennas 104 are receiving. For example, the receiving antennas 110 are receiving and, in some implementations, the first transmitting antenna 106 may also be receiving during the back baseline sweep. In doing so, a set of back-scan baseline transmission coefficient values or voltage values are obtained, including $|S_{N-1}|_b$, $|S_{N-2,N}|_b$ . . . $|S_{1,N}|_b$.

In various implementations, the reflection coefficient or voltage values obtained in the front and back baseline sweeps 402, 404 of <−10 dB are achieved for all of the receiving antennas 110 at 915 MHz, for example.

At 406, a front sweep for starting point identification is performed. The subject/phantom is placed upon the biometric monitoring sensor 100 during the front sweep, and the aim is to identify a starting point location of the subject/phantom. In the front sweep, the first transmitting antenna 106 is transmitting, while the rest of the antennas in the array of antennas 104 are receiving. Transmission coefficient or voltage measurements are sequentially obtained, starting with an immediately adjacent one of the receiving antennas 110 to the first transmitting antenna 106 ($|S_{2,1}|$), and moving on up to an antenna I ($|S_{I,1}|$). Here, antenna I refers to the first antenna that exhibits a threshold difference in a transmission coefficient value or voltage value as compared to its corresponding front-scan baseline transmission coefficient value or voltage value determined at 402. In an example, the threshold difference for the aforementioned transmission coefficient values is >5 dB in absolute value. Antenna I is identified as the starting point of the subject/phantom upon the biometric monitoring sensor 100.

At 408, a back sweep for ending point identification is performed. The subject/phantom remains upon the biometric monitoring sensor 100, and the aim is to identify an ending point location of the subject/phantom. In the back sweep, the second transmitting antenna 108 is transmitting, while the rest of the antennas in the array of antennas 104 are receiving. Transmission coefficient or voltage measurements are sequentially obtained, starting with an immediately adjacent one of the receiving antennas 110 to the second transmitting antenna 106 ($|S_{N-1,N}|$), and moving on up to and antenna J ($|S_{J,N}|$, where J>I). Here, antenna J refers to the first antenna that exhibits the threshold difference in a transmission coefficient value or voltage value as compared to its corresponding back-scan baseline transmission coefficient value or voltage value determined at 404. Antenna J is identified as the ending point of the subject/phantom upon the fabric. The length of the subject (or, equivalently, the length of the phantom) can eventually be calculated as:

$$\text{Length} = [(J - I) + 1] \times d, \qquad \text{Equation (1)}$$

where J is an antenna number identified in the back sweep 408 in the receiving antennas 110 (as ordered from the first transmitting antenna 106 to the second transmitting antenna 108), I is an antenna number identified in the front sweep 406 in the receiving antennas 110, and d is the predetermined distance 112 between antennas in the array of antennas 104.

While specific examples are provided above for instantaneous biometric readings (e.g., length/height, weight, mood) of a subject, in various implementations, the biometric readings may be obtained periodically. For example, when incorporated into fitted crib sheets in the infant's sleep environment, the biometric readings may be performed periodically while the infant is sleeping to detect a change in motion associated with increased risk for SIDS. The periodic biometric readings may be measured in near real-time/continuous monitoring or at a predetermined delay interval, such as every minute, every five minutes, or some other delay interval.

To detect motion, the periodic biometric readings may detect that the antenna number of the I and/or J antenna are different from one reading to a subsequent reading. When the pressure sensor 118 is present, motion may additionally be detected by detecting periodic changes in the pressure measurement. An alert may be triggered if no motion is detected within a predetermined motion period.

When multiple arrays of antennas are used, the periodic monitoring may additionally be used to detect the position and orientation of a subject. Therefore, the biometric monitoring sensor(s) described herein may be used to detect when an infant has rolled over in their sleep, positioned themselves too close to an edge of the biometric monitoring sensor, or otherwise detect an undesired orientation of a subject.

Figure 5A:
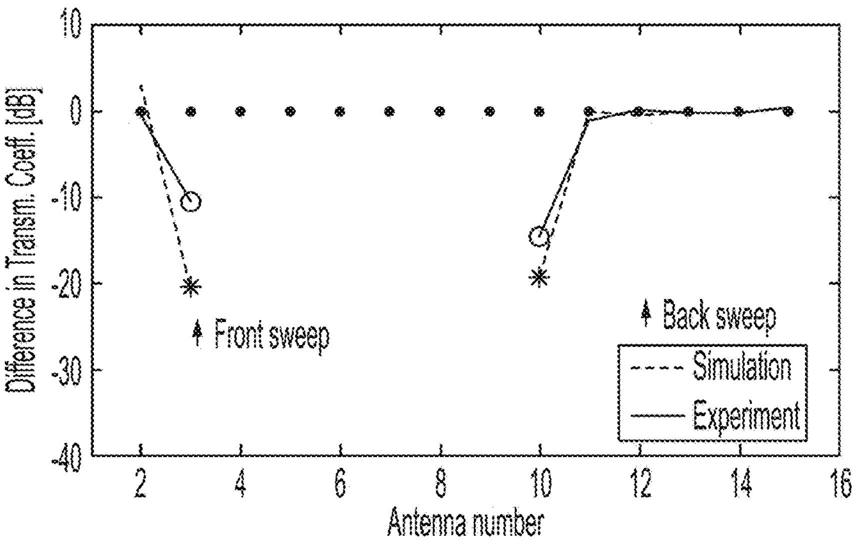
FIG. 5A-5C are experimental results of operation of the biometric monitoring sensor.
Figure 5B:
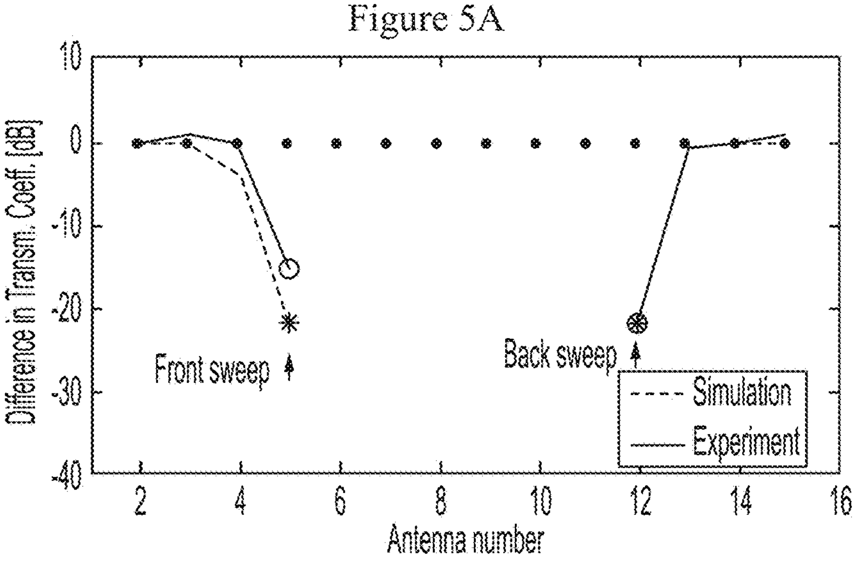
Figure 5C:
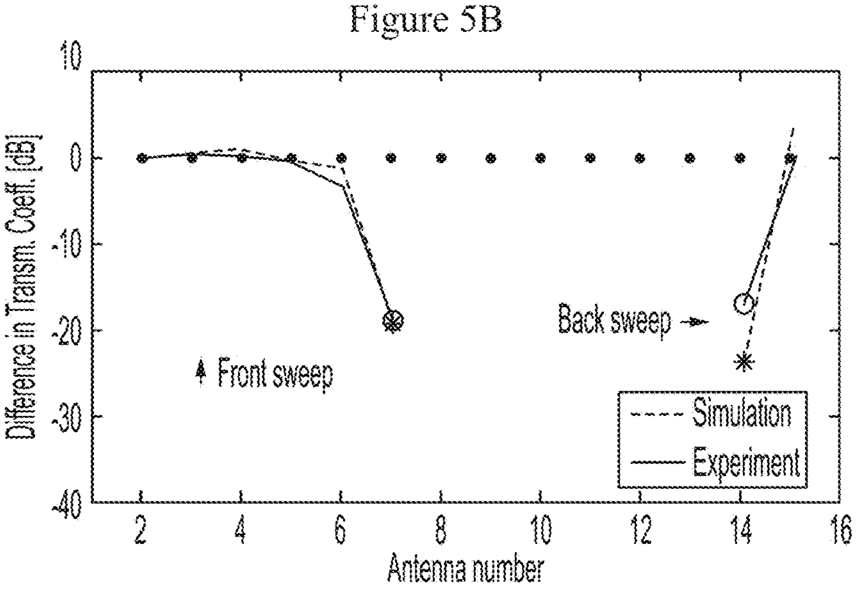

FIG. 5A-5C are experimental results of operation of the biometric monitoring sensor 200. In the experimental results, a phantom with the formulation of Table I is emulated as a square-footprint box, occupying a surface area of 16 cm×16 cm, and exhibiting properties equal to the average of human tissues at 915 MHz ($\varepsilon r=56.8$, $\sigma=1.07$ S/m). In an attempt to simulate a worst-case scenario, the phantom's thickness is selected to be equal to only 1 cm. Expectedly, thicker phantoms are anticipated to exhibit much more pronounced differences between the intended transmission coefficient values or voltage values. The 0.5-mm gap between the fabric 102 and the phantom introduced by the container itself is negligible and can rather emulate the presence of clothing worn by the subject. Simulations for even thicker gaps have indicated no deterioration in the achieved performance. Radiation boundaries were set at a distance of >λ/4 away from the structure (free space wavelength at 915 MHz (λ) 32.7 cm, implying that λ/4~=8 cm).

In order to ensure that the phantom's length can be accurately retrieved, regardless of its exact position upon the biometric monitoring sensor 200, three scenarios were tested in both simulations and measurements. In a first scenario, shown in FIG. 5A, the phantom was placed near the top of the biometric monitoring sensor 200, blocking antennas #3 to #10. In a second scenario, shown in FIG. 5B, the phantom was placed approximately in the middle of the biometric monitoring sensor 200, blocking antennas #5 to #12. In a third scenario, shown in FIG. 5C, the phantom was placed near the end of the biometric monitoring sensor 200, blocking antennas #7 to #14.

In each of FIGS. 5A-5C, both measurement and simulation results are super-imposed for all three scenarios. Notably, insignificant discrepancies are observed between simulations (dotted lines) and in-vitro experimental results (solid lines). The plots in FIGS. 5A-5C show the difference in the transmission coefficient values between the baseline case vs. the case where the phantom lies upon the biometric monitoring sensor 200 for both the front baseline sweep 402 and back baseline sweep 404, described above. The starting and ending points of the phantom can be clearly identified by the antenna location in each sweep where the transmission coefficient exhibits greater than a threshold difference. As discussed above, the threshold difference between the transmission coefficients is greater than 5 dB for identifying the starting and ending points of the phantom.

As shown in FIG. 5A, the simulation and measurement results both indicate that the phantom extends between dipoles #3 and #10. As such, and based on Equation (1), the length of the phantom is found to be equal to 16 cm, which is indeed the case. Similarly, in FIG. 5B, the simulation and measurement results both indicate that the phantom extends between dipoles #5 and #12. In FIG. 5C, the simulation and measurement results both indicate that the phantom extends between dipoles #7 and #14. In all of the above examples, Equation (1) again indicates that the correct phantom length of 16 cm is determined. Therefore, regardless of the position on the biometric monitoring sensor 200, the correct length of the phantom is determined based on detecting the starting and ending points of the phantom on the biometric monitoring sensor 200. The resolution was as high as 2 cm, as dictated by the employed antenna separation distance on the biometric monitoring sensor 200.

Notably, this recumbent length detection capability is not limited in any way by the exact placement of the phantom upon the biometric monitoring sensor 200 (e.g., phantom placed in the middle of the fabric vs. phantom placed towards the edge of the fabric). Even more importantly, the biometric monitoring sensors 100, 200, 300 are scalable to any desired size and any desired accuracy.

Figure 6A:
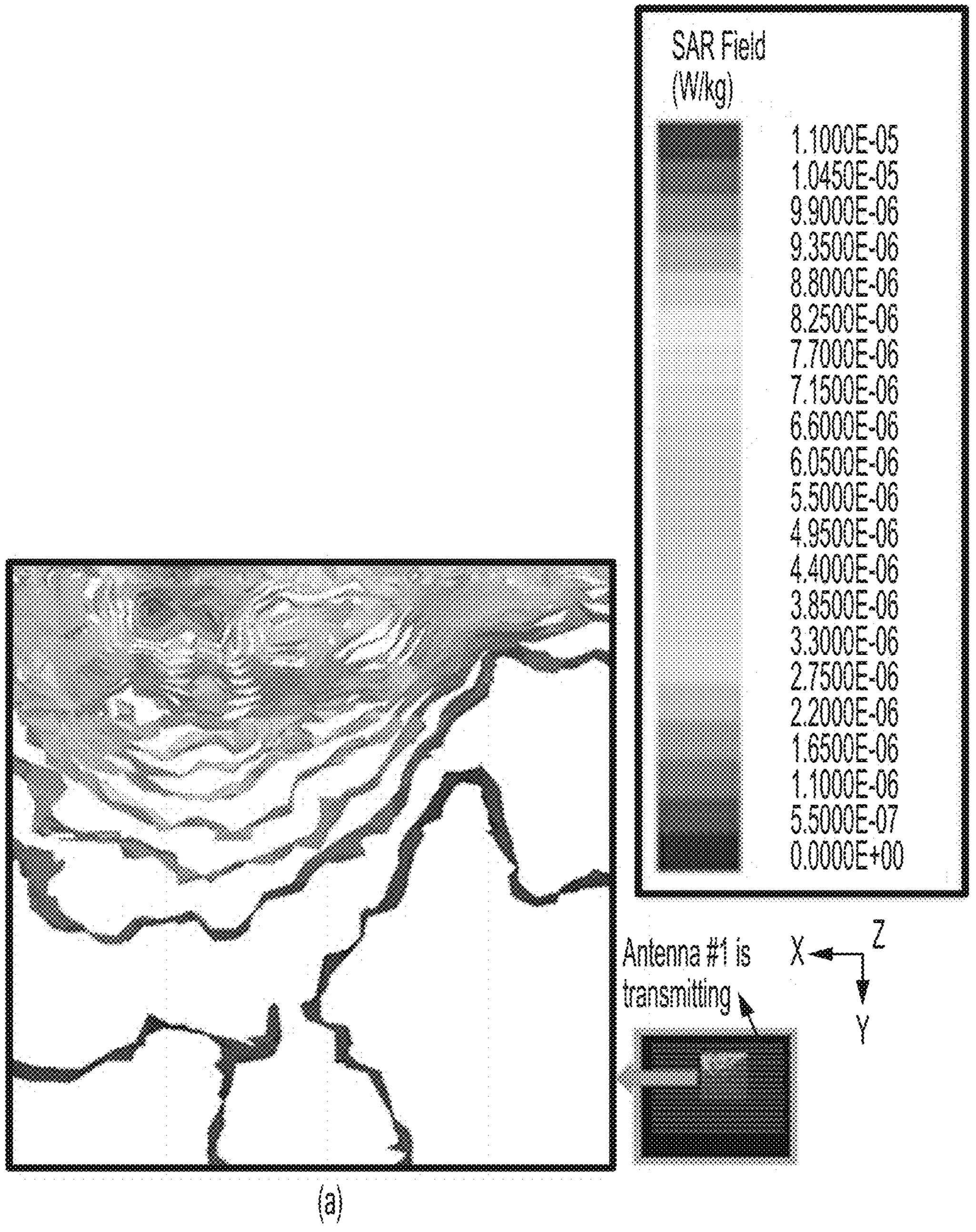
FIGS. 6A-6B are plots of the specific absorption rate of a phantom body during antenna transmission.
Figure 6B:
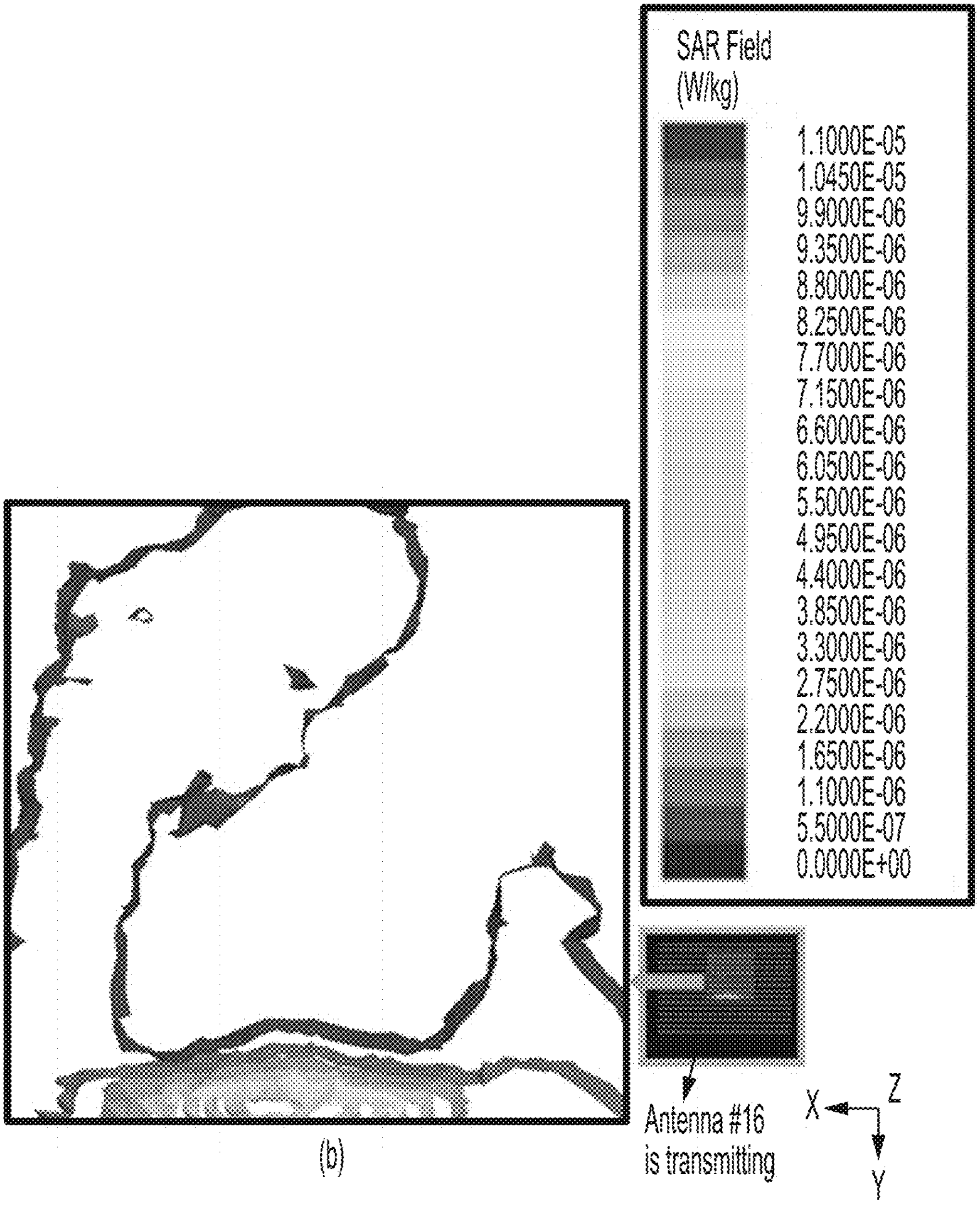

FIGS. 6A-6B are plots of the specific absorption rate of a phantom body during antenna transmission. Specific absorption rate (SAR) performance and conformance to Federal Communications Commission (FCC) guidelines for human safety are achieved by the biometric monitoring sensor 200. The FCC safety guidelines for human exposure to electromagnetic fields limit the SAR averaged over any 1 gr of tissue to SAR1g<1.6 W/kg. With this in mind, SAR simulations were performed to evaluate compliance of biometric monitoring sensor 200. To do so, the phantom mass density was set to 1.04 gr/$cm^3$, and the antenna input power was set to 10 μW to match the corresponding power level in testing the biometric monitoring sensor 200.

Both the front sweep, shown in FIG. 6A, and back sweep, shown in FIG. 6B demonstrate, expectedly, higher $SAR_{1g}$ values at the areas closer to the corresponding transmitting antennas. As shown, the biometric monitoring sensor 200 can operate at 10 μW input power, implying ~105 times lower $SAR_{1g}$ than that recommended by FCC.

It should be appreciated that the logical operations described herein with respect to the various figures may be implemented (1) as a sequence of computer implemented acts or program modules (i.e., software) running on a computing device (e.g., the computing device described in FIG. 9), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Figure 7:
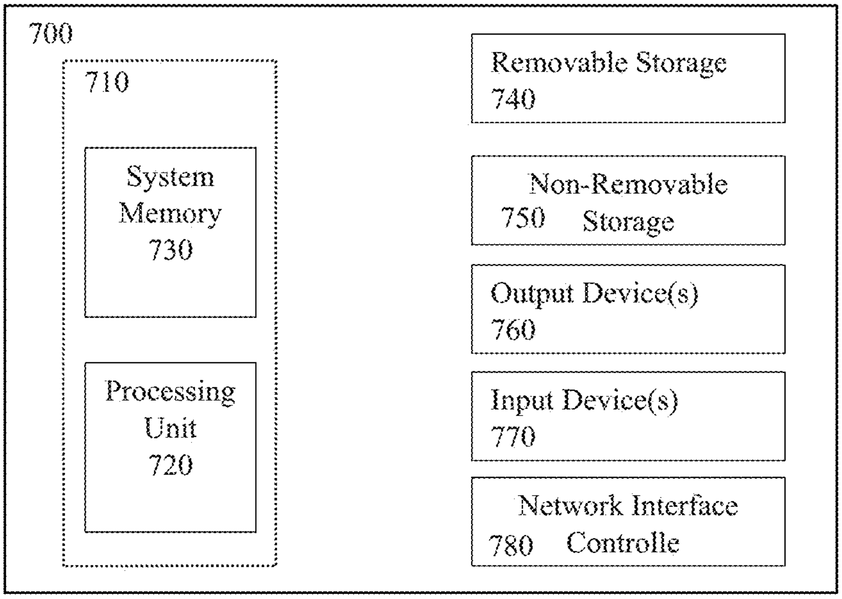
FIG. 7 is an example computing device upon which embodiments of the invention may be implemented.

Referring to FIG. 7, an example computing device 700 upon which embodiments of the invention may be implemented is illustrated. For example, the microcontroller 320 or external device described herein may each be implemented as a computing device, such as computing device 700. It should be understood that the example computing device 700 is only one example of a suitable computing environment upon which embodiments of the invention may be implemented. Optionally, the computing device 700 can be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In an embodiment, the computing device 700 may comprise two or more computers in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. In an embodiment, virtualization software may be employed by the computing device 700 to provide the functionality of a number of servers that is not directly bound to the number of computers in the computing device 700. For example, virtualization software may provide twenty virtual servers on four physical computers. In an embodiment, the functionality disclosed above may be provided by executing the application and/or applications in a cloud computing environment. Cloud computing may comprise providing computing services via a network connection using dynamically scalable computing resources. Cloud computing may be supported, at least in part, by virtualization software. A cloud computing environment may be established by an enterprise and/or may be hired on an as-needed basis from a third party provider. Some cloud computing environments may comprise cloud computing resources owned and operated by the enterprise as well as cloud computing resources hired and/or leased from a third party provider.

In its most basic configuration, computing device 700 typically includes at least one processing unit 720 and system memory 730. Depending on the exact configuration and type of computing device, system memory 730 may be volatile (such as random access memory (RAM)), non-volatile (such as read-only memory (ROM), flash memory, etc.), or some combination of the two. This most basic configuration is illustrated in FIG. 7 by dashed line 710. The processing unit 720 may be a standard programmable processor that performs arithmetic and logic operations necessary for operation of the computing device 700. While only one processing unit 720 is shown, multiple processors may be present. Thus, while instructions may be discussed as executed by a processor, the instructions may be executed simultaneously, serially, or otherwise executed by one or multiple processors. The computing device 700 may also include a bus or other communication mechanism for communicating information among various components of the computing device 700.

Computing device 700 may have additional features/functionality. For example, computing device 700 may include additional storage such as removable storage 740 and non-removable storage 750 including, but not limited to, magnetic or optical disks or tapes. Computing device 700 may also contain network connection(s) 780 that allow the device to communicate with other devices such as over the communication pathways described herein. The network connection(s) 780 may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards such as code division multiple access (CDMA), global system for mobile communications (GSM), long-term evolution (LTE), worldwide interoperability for microwave access (WiMAX), and/or other air interface protocol radio transceiver cards, and other well-known network devices. Computing device 700 may also have input device(s) 770 such as a keyboards, keypads, switches, dials, mice, track balls, touch screens, voice recognizers, card readers, paper tape readers, or other well-known input devices. Output device(s) 760 such as a printers, video monitors, liquid crystal displays (LCDs), touch screen displays, displays, speakers, etc. may also be included. The additional devices may be connected to the bus in order to facilitate communication of data among the components of the computing device 700. All these devices are well known in the art and need not be discussed at length here.

The processing unit 720 may be configured to execute program code encoded in tangible, computer-readable media. Tangible, computer-readable media refers to any media that is capable of providing data that causes the computing device 700 (i.e., a machine) to operate in a particular fashion. Various computer-readable media may be utilized to provide instructions to the processing unit 720 for execution. Example tangible, computer-readable media may include, but is not limited to, volatile media, non-volatile media, removable media and non-removable media implemented in any method or technology for storage of information such as computer readable instructions, data structures, program modules or other data. System memory 730, removable storage 740, and non-removable storage 750 are all examples of tangible, computer storage media. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

It is fundamental to the electrical engineering and software engineering arts that functionality that can be implemented by loading executable software into a computer can be converted to a hardware implementation by well-known design rules. Decisions between implementing a concept in software versus hardware typically hinge on considerations of stability of the design and numbers of units to be produced rather than any issues involved in translating from the software domain to the hardware domain. Generally, a design that is still subject to frequent change may be preferred to be implemented in software, because re-spinning a hardware implementation is more expensive than re-spinning a software design. Generally, a design that is stable that will be produced in large volume may be preferred to be implemented in hardware, for example in an application specific integrated circuit (ASIC), because for large production runs the hardware implementation may be less expensive than the software implementation. Often a design may be developed and tested in a software form and later transformed, by well-known design rules, to an equivalent hardware implementation in an application specific integrated circuit that hardwires the instructions of the software. In the same manner as a machine controlled by a new ASIC is a particular machine or apparatus, likewise a computer that has been programmed and/or loaded with executable instructions may be viewed as a particular machine or apparatus.

In an example implementation, the processing unit 720 may execute program code stored in the system memory 730. For example, the bus may carry data to the system memory 730, from which the processing unit 720 receives and executes instructions. The data received by the system memory 730 may optionally be stored on the removable storage 740 or the non-removable storage 750 before or after execution by the processing unit 720.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

Embodiments of the methods and systems may be described herein with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A system for measuring growth of an individual; wherein the system comprising:

a substrate having a first dimension and a second dimension;

an array of a plurality of antennas coupled to the substrate, the plurality of antennas comprising a first set of parallel, elongate antennas each extending across the substrate in the first dimension and being spaced apart from an adjacent antenna of the first set in the second dimension by a predetermined distance, and a second set of parallel, elongate antennas each extending across the substrate in the second dimension and being spaced apart from an adjacent antenna of the second set in the first dimension by the predetermined distance; wherein each of the plurality of pairs of antennas includes a transmitting antenna and a receiving antenna;

wherein the plurality of pairs of antennas includes a first pair and a second pair, the first pair including a transmitting antenna and a first receiving antenna, and the second pair including the transmitting antenna and a second receiving antenna different from the first receiving antenna; and a controller configured to determine the growth of the individual in contact with the substrate, wherein for each of a plurality of pairs of antennas in the array of the plurality of antennas, the controller is configured to supply a first signal to a first one of the plurality of antennas and to measure an electromagnetic property of the first signal received at the second one of the plurality of antennas, wherein the growth of the individual in contact with the substrate is determined based on identification of locations of one or more of the pairs of antennas where the measured electromagnetic property is greater than a threshold.

2. The system of claim 1, wherein each of the plurality of antennas is a conductive trace.

3. The system of claim 1, wherein the substrate is flexible.

4. The system of claim 1, wherein the measured electromagnetic property is greater than the threshold when a difference between the measured electromagnetic property and an expected electromagnetic property is greater than a second threshold.

5. The system of claim 1, wherein the electromagnetic property is a transmission coefficient or voltage of the first signal.

6. The system of claim 1, wherein the transmitting antenna is at a first end of the first dimension of the substrate.

7. The system of claim 1, wherein the controller is configured to identify a first receiving antenna where the measured electromagnetic property is greater than a threshold.

8. The system of claim 1, wherein for different ones of the plurality of pairs of antennas, the transmitting antenna is a different one of the plurality of antennas.

* * * * *